United States Patent [19]
Kaufman et al.

[11] Patent Number: 5,155,435
[45] Date of Patent: Oct. 13, 1992

[54] METHOD AND APPARATUS FOR PERFORMING INTERVENTIONAL MEDICAL PROCEDURES USING MR IMAGING OF INTERVENTIONAL DEVICE SUPERIMPOSED WITH GHOST PATIENT IMAGE

[75] Inventors: Leon Kaufman, San Francisco; David M. Kramer, San Rafael; Christine Hawryszko, San Mateo, all of Calif.

[73] Assignee: The Regents of the University of California, Oakland, Calif.

[21] Appl. No.: 741,943

[22] Filed: Aug. 8, 1991

[51] Int. Cl.⁵ .............................................. G01R 33/20
[52] U.S. Cl. .................................................... 324/309
[58] Field of Search ................ 364/413; 324/300, 307, 324/308, 309, 310, 311, 312, 313, 314, 318, 322; 128/653 A, 653 SC

[56] References Cited

U.S. PATENT DOCUMENTS 4,674,046  6/1987  Ozeki et al. .......................... 324/312
4,994,965  2/1991  Crawford et al. ................... 364/413

*Primary Examiner*—Michael J. Tokar
*Attorney, Agent, or Firm*—Nixon & Vanderhye

[57] ABSTRACT

Positioning of interventional devices within the patient image volume of an MRI system is performed while viewing real-time fluoroscopic MR images of such devices superimposed upon a saved prior image ("ghost") of patient anatomy that was earlier located within the same image volume. After such interventional medical procedure is thoroughly planned using the earlier acquired three-dimensional ghost image, the patient anatomy is relocated within the image volume and the final selected trajectory for the interventional device or medical procedure is then performed (preferably while real time MRI fluoroscopy is used to monitor the actual interventional procedure within the real patient anatomy).

34 Claims, 9 Drawing Sheets

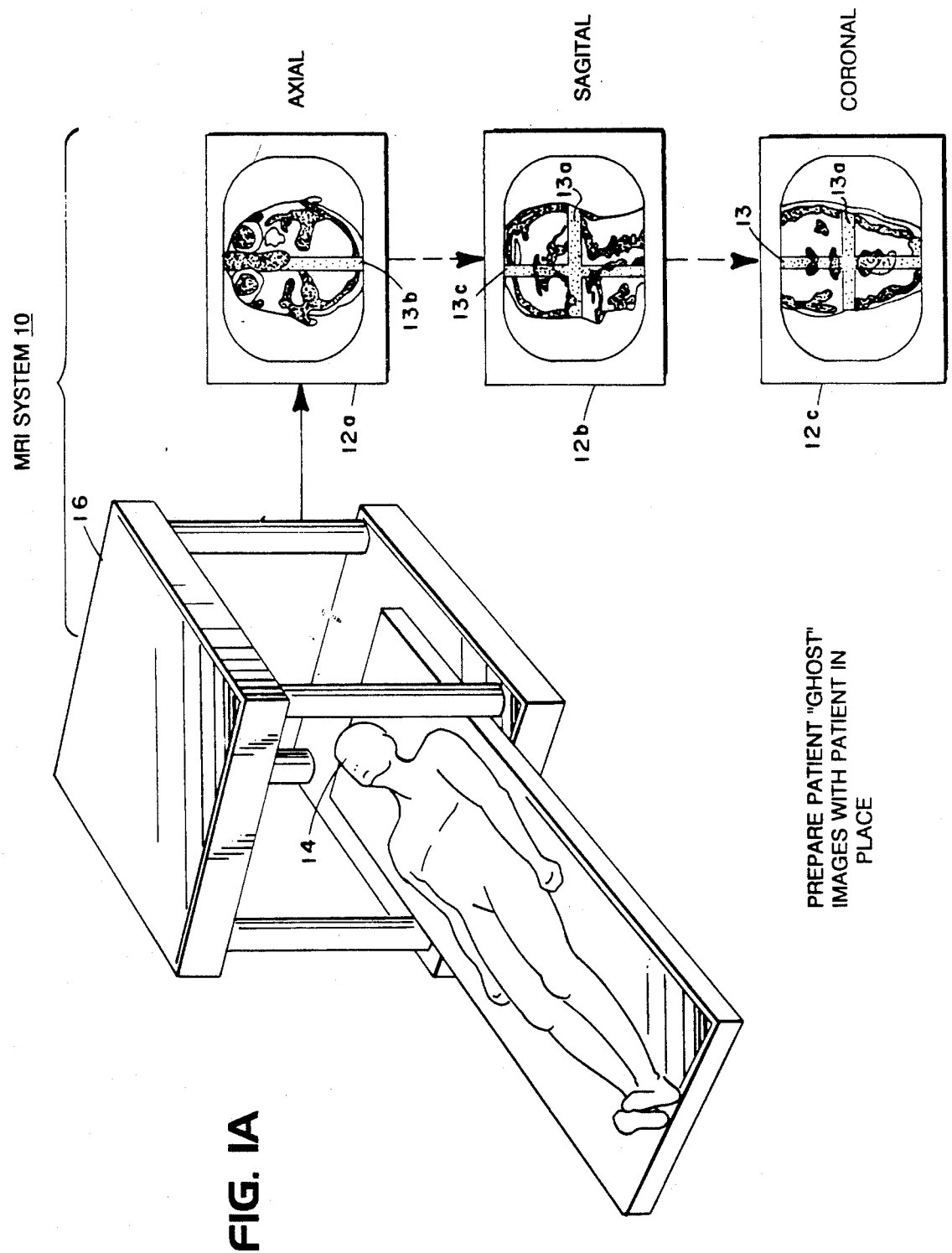

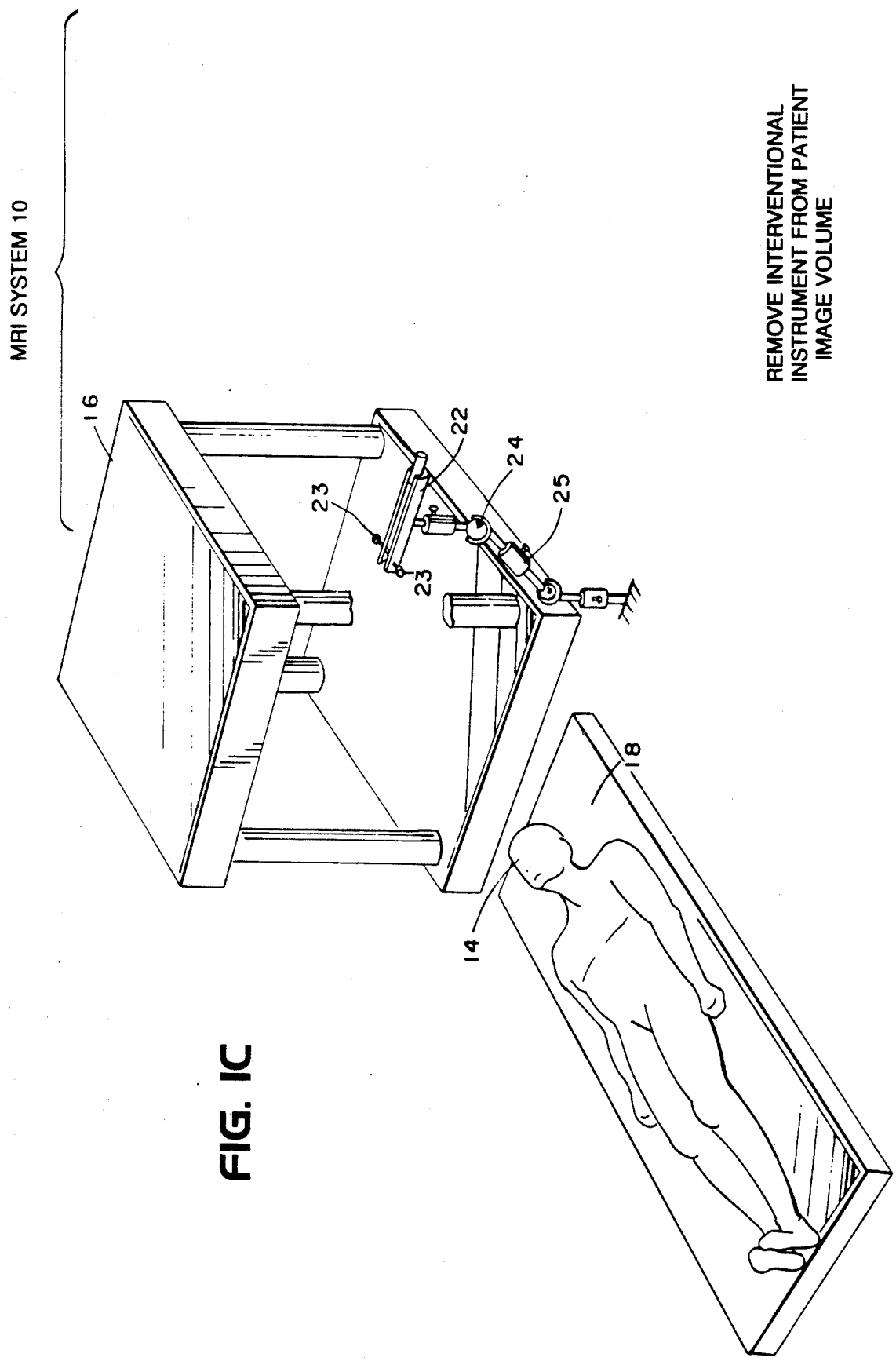

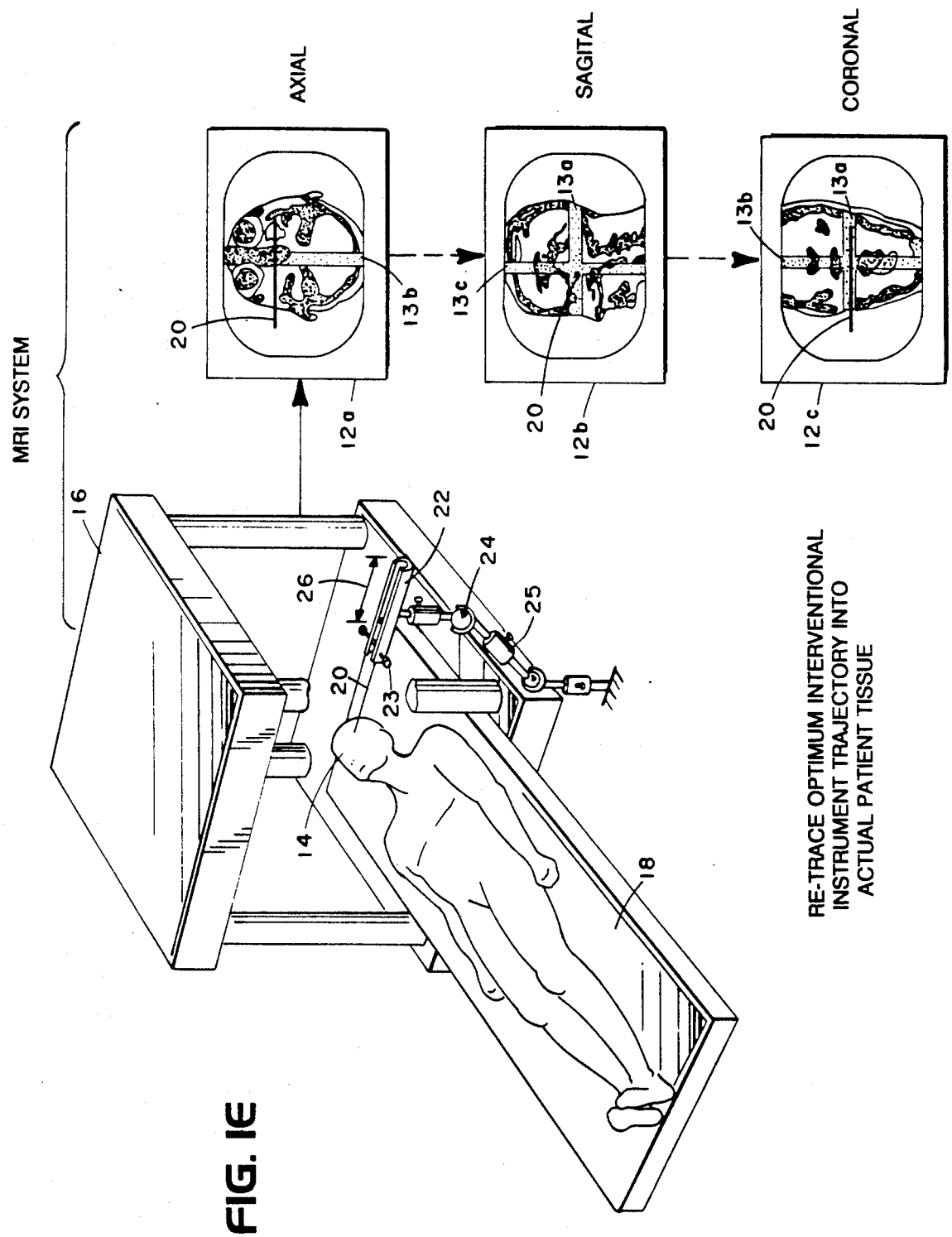

METHOD AND APPARATUS FOR PERFORMING INTERVENTIONAL MEDICAL PROCEDURES USING MR IMAGING OF INTERVENTIONAL DEVICE SUPERIMPOSED WITH GHOST PATIENT IMAGE

BACKGROUND OF THE INVENTION

1. Field of the Invention

This invention is generally related to the field of magnetic resonance imaging (MRI) utilizing nuclear magnetic resonance (NMR) phenomena. It is more particularly directed to method and apparatus for efficiently and safely planning and performing interventional medical procedures using MR imaging of interventional device(s) and of relevant patient anatomy.

2. Related Applications

This application is related to commonly assigned copending U.S. application Ser. No. 07/650,215 filed Feb. 4, 1991 entitled "Real Time MR Imaging Inside Gantry Room" and naming Kaufman, Arakara, Kramer, McCarten and Hawryszko as inventors. The entire content of such prior related application is hereby incorporated by reference.

3. Description of Related Art

Modern MRI systems now include some with magnet structures that provide rather free and open lateral access to the patient image volume during MRI procedures. For example, the ACCESS® low field MRI system available from Toshiba Corporation is such a system. Such open magnet architecture and MRI-compatible interventional instruments have already been recognized as greatly facilitating the use of MRI in interventional procedures. See, for example, Dietrich et al, "Low-Field Design Eases MRI-Guided Biopsies," *Diagnostic Imagino*, pages 139–143, March 1991. Real time fluoroscopy MRI is now also known and is expected to soon become commercially available. The above-identified related copending application describes such real time MRI fluoroscopy with provisions for including the MR image display inside the gantry room thus further facilitating use of MRI in interventional procedures.

Interventional procedures (e.g., biopsy, treatment, stereotaxy) require placement of various devices in or around the patient body. For example, even the introduction of a simple needle deeply within the human anatomy requires the attending physician to carefully plan the needle trajectory (e.g., angle, depth of penetration, etc.) so as to reach the desired end point with a minimum of damage to intervening tissues. In short, it is important that the interventional devices properly avoid certain parts of the patient anatomy while it is just as important that the device (or at least the active portion of the device) accurately reach, penetrate, etc. other particular portions of the patient anatomy. Even when real time fluoroscopic MRI is used as an aid in this process, the process requires apriori decision making and typically results in relatively slow procedure execution.

Of course it has long been known to use prior images of relevant patient anatomy (e.g., X-ray, CT Scans, MRI, etc) for the attending physician to study in advance to plan an optimum trajectory for the interventional device. However, inherent inaccuracies in the MRI process make such planning quite difficult if not impossible using MRI. Furthermore, due to common mis-perceptions in the medical community about absolute accuracy of MRI, such planning can even be deceptive.

In particular, although MRI provides very good relative information about tissue structure and location, it inherently can never provide absolute dimensional accuracy for interventional procedures planned on the basis of mere inspection of prior MR images of patient anatomy alone. In effect, the dimensional scale of an MR image changes from point-to-point throughout the image in a complex and somewhat unpredictable way. Thus, merely measuring the distance between two points on the two-dimensional image surface does not mean that the measured distance will correspond to the actual distance between those two indicated points of the anatomy within the human body. It can perhaps be analogized to the drawing of an image on a rubber sheet which is then deflected so as to be non-planar. A two-dimensional projection of such a distorted rubber sheet image does not provide a constant scale image on which accurate absolute dimensions can be measured.

Even though absolute dimensional accuracy is not possible using MR images, the relative location of objects within an MR image can be highly accurate. Thus, if the image shows two structures intersecting, it can be safely assumed that they actually do intersect. Similarly, if they do not intersect in the image, then it can be safely assumed that they do not intersect.

BRIEF SUMMARY OF THE INVENTION

We propose new method and apparatus for planning and later effecting interventional medical procedures using MR imaging. In particular, we propose the superposition of previously acquired patient anatomy MR images (i.e., a "ghost") and real-time MR images of an interventional device. Alternatively, it may be desirable in some circumstances to superimpose a previously acquired MR image of the interventional device (i.e., a device "ghost") with real-time MR images of the patient anatomy.

In an exemplary embodiment, the relevant patient anatomy is placed within the image volume of an MRI system and imaged. The captured image is stored for later recall and superimposition with other images in an "averaging" mode, e.g., wherein MRI display data are not refreshed (i.e., completely replaced each frame) as in normal MRI fluoroscopy but, rather, are added to future images. When the patient table is rolled out of the image volume, an MR-visible needle or other interventional device of choice can be introduced into the patient volume and its trajectory observed in superposition with the previously acquired patient image or "ghost." In the "averaging" mode, the image of the needle will continue to build over the patient ghost as time progresses. The attending physician can try various alternate trajectories until an optimum desired trajectory is found. An appropriate mechanical jig (e.g., including clampable universal joints, predefined slideable tracks, etc.) supports the interventional device from a region outside the patient's body (and perhaps at least partially outside the image volume of the MRI system). Such a jig also permits the desired trajectory to be effectively "remembered" and retraced at some later time when the supporting jig is locked into position with the appropriate support angles, etc. The length of needle extension, etc., may also be suitably noted, marked, delimited (e.g., with a clampable stop structure) so as to permit easy retracing of the desired trajectory.

As those in the art will appreciate, MR-visible interventional devices can be suitably devised. They are preferably formed mostly of non-magnetic materials. If the material itself is not already MR-visible, then the device may be filled with an MR-visible fluid (e.g., oil, suitably doped water, etc.) or surrounded by a sleeve which contains an MR-visible fluid so as to make the interventional device clearly visible when imaged in superposition with a patient ghost image. When the MRI system continues to be operated in an averaging mode, the image of the interventional device will continue to build in intensity over the superimposed patient ghost the longer it remains in a certain position.

Once the desired trajectory of the interventional device has been located, then the supporting jig apparatus is suitably locked into position and the interventional device is retracted from the imaging volume. Thereafter, the patient anatomy is reintroduced and fresh MR images are taken to confirm that the patient anatomy is back in the same nominal position. This may include, for example, superimposing the prior patient "ghost" image with the current real time patient image until they are coincident. It can also be accomplished by the attending physician noting the location of particular structures of interest within the current MR images as coinciding with the locations noted earlier when the original ghost image was taken. Yet further, the relevant patient anatomy may in some circumstances be suitably immobilized on the movable patient bed which can then be accurately mechanically repositioned at the same location within the patient image volume of the MRI system.

Once the resumed patient position is confirmed as coinciding with the original position (i.e., during acquisition of the prior ghost images), then the interventional device can be caused to relatively quickly retrace the earlier located optimum trajectory with added assurance that it will avoid critical anatomic areas while at the same time finding the desired critical anatomic areas. Similar procedures can be used for placement/use of stereotatic devices as should now be apparent to those in the art.

Using this invention, the attending physician is afforded an interactive capability that simulates real time trial and error procedures on the patient anatomy—but without any danger or discomfort to the real patient anatomy. This technique also automatically compensates for inherent MRI system inaccuracies caused by field and gradient non-uniformities. As previously noted, such inherent inaccuracy in MRI cannot be easily compensated by merely making measurements on MR images of patient anatomy. Furthermore, for convenience, a template image of the patient anatomy or of the mechanical interventional device can be saved and restored for many trial procedures without the need to actually reintroduce one or the other into the image volume.

Thus this invention provides pseudo real-time positioning of needles, therapeutic or stereotatic devices within or on a patient image "ghost" (i.e., while the patient is removed from the image volume). Reusable template images are also available for convenience when many trial and error steps are required.

BRIEF DESCRIPTION OF THE DRAWINGS

These as well as other objects and advantages of this invention will be more completely understood and appreciated by careful study of the following more detailed description of presently preferred exemplary embodiments of this invention taken in conjunction with the accompanying drawings, of which:

FIGS. 1A, 1B, 1C, 1D and 1E schematically depict successive steps in an interventional medical procedure using an exemplary embodiment of this invention;

DESCRIPTION OF EXEMPLARY EMBODIMENT

Figure 1B:
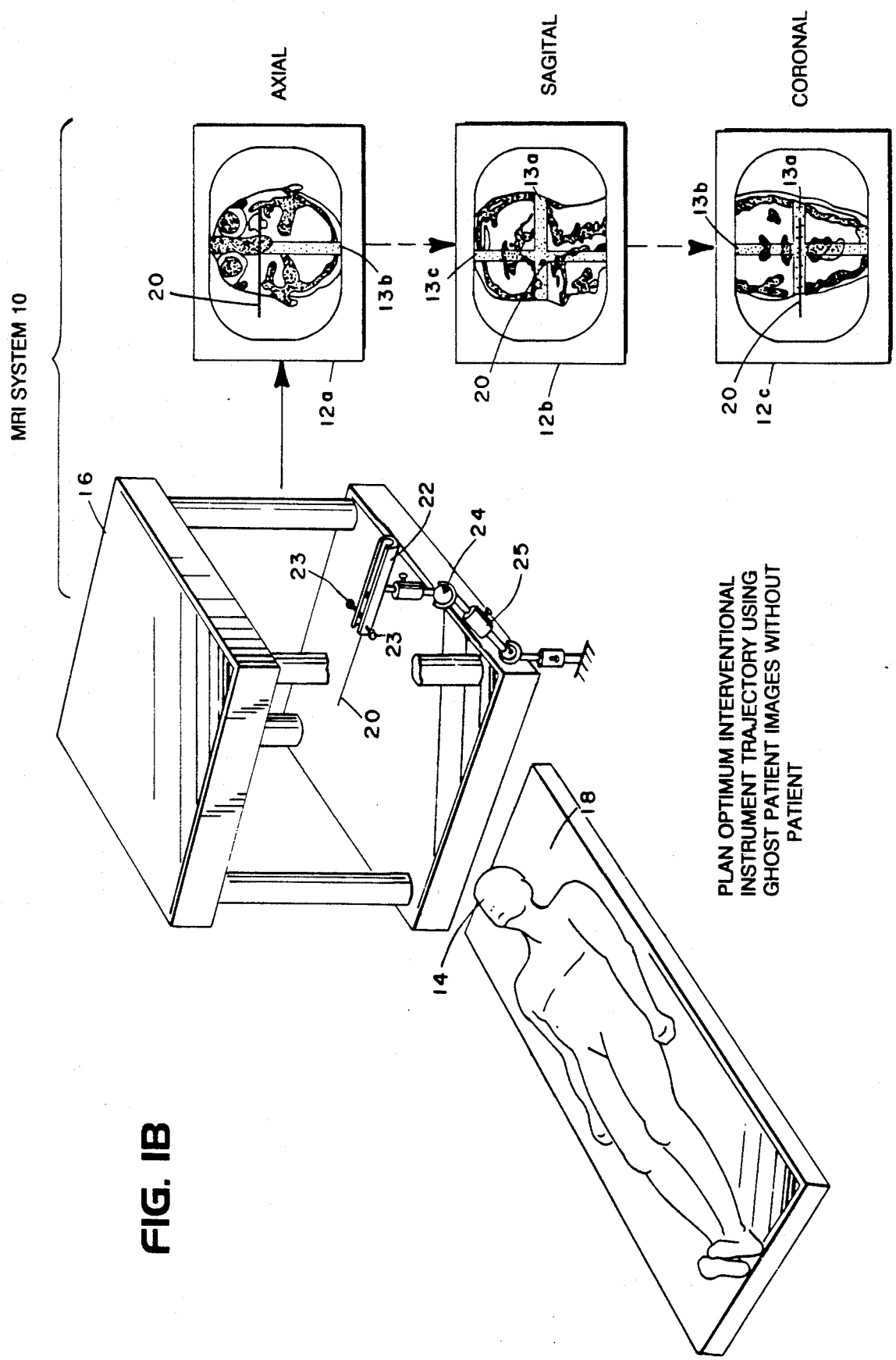

The MRI system 10 depicted in FIGS. 1A-1E includes the usual control/imaging computers, magnet gantry, gradient coils, RF coils, RF circuits, digital memory, etc. It is preferably of an open magnet architecture (e.g., so as to permit lateral access to the patient image volume by an attending physician). Furthermore, the displayed MR images 12a 12b, 12c are preferably displayed within the gantry room for easy observation by the attending physician. As those in the art will appreciate, the usual axial, sagital and coronal views of patient anatomy within the image volume may actually appear simultaneously on a common screen display. Furthermore, the control/imaging computer of the MRI system 10 is modified so as to provide an apparatus which is capable of superimposing previously acquired images with ongoing real-time images (i.e., real-time fluoroscopy in an "averaging" mode superimposed with a prior stored image). (The stippled linear bands 13a, 13b, 13c included in the image are the usual added locators of the axial, sagital and coronal image planes 12a, 12b, 12c, respectively, as will be recognized.)

The first step of an exemplary interventional medical procedure is depicted at FIG. 1A. Here, the desired patient anatomy 14 is placed within the image volume of the MRI system magnet 16. Once the attending physician is satisfied that the correct portion of the patient anatomy is properly placed within the image volume for effecting the desired interventional procedure, a suitable set of "ghost" images 12a, 12b, 12c are memorized for future use.

Thereafter, the patient anatomy 14 is rolled out of the image volume on the usual patient bed 18 (typically mounted on linear roller tracks). Then, as depicted in FIG. 1B, an interventional device (e.g., needle 20) is introduced into the image volume of the MRI system. As schematically depicted, its trajectory track is guided by a suitable retractable track or guiding pathway 22 which can be positioned as desired via one or more clampable universal joints 24, linear slide joints 25, stops 23 or other clampable jig structures as may be desired. An optimum interventional instrument trajectory may then be planned by superimposing real time fluoroscopy MRI of the instrument 20 with the previously acquired patient ghost images. Different trajectories can be tried as often as desired until the desired optimum trajectory is selected and effectively memorized by suitable clamping of the jig structures 22, 24, 25, etc. As will be appreciated, the images appearing during this planning stage of the procedure will appear to depict the needle 20 actually entering into the three-dimensional patient anatomy—even though the real patient anatomy is completely removed from the image volume at this time.

Figure 1D:
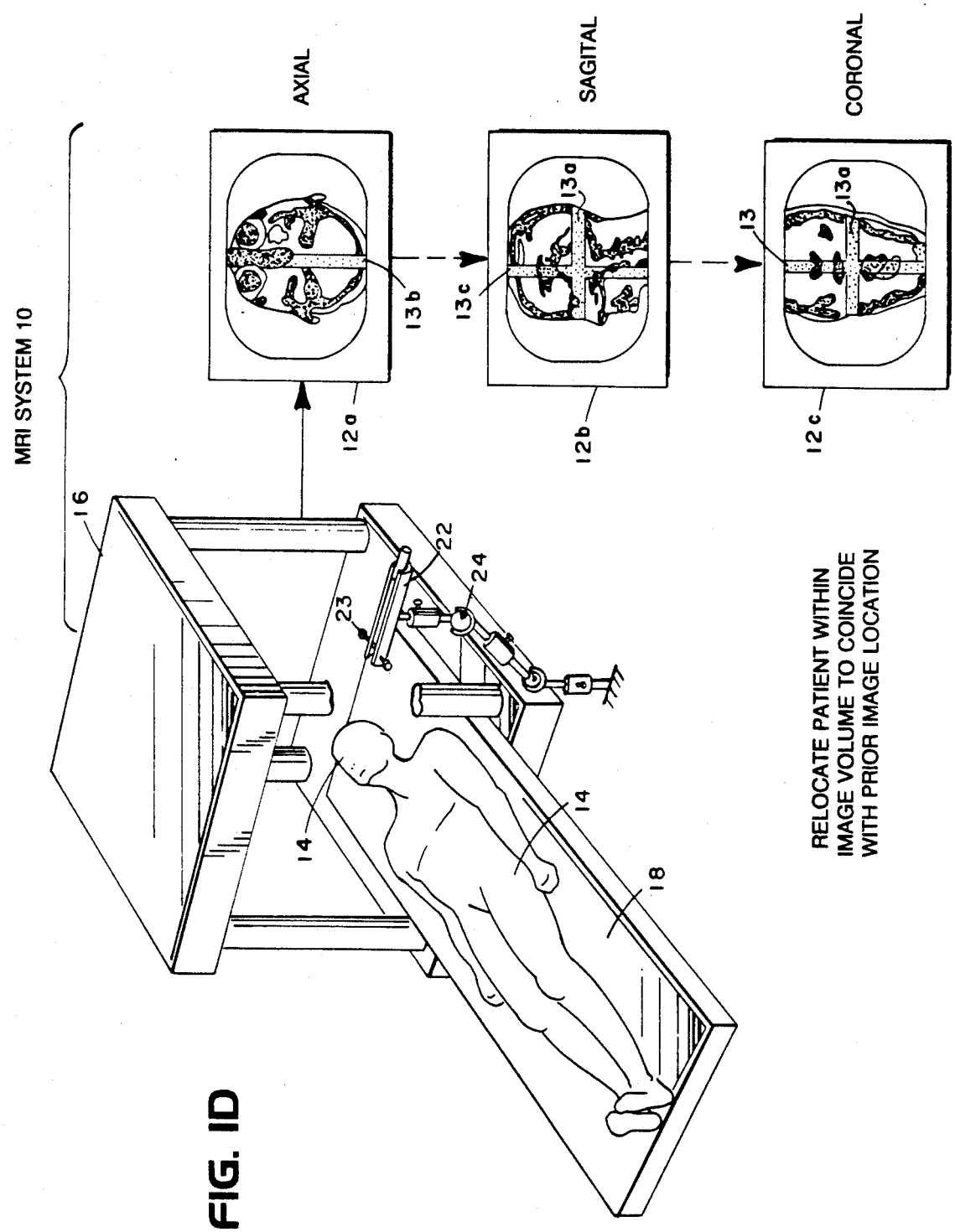

Subsequently, the instrument is also removed from the patient image volume as depicted at FIG. 1C and the patient is relocated within the image volume as depicted in FIG. 1D so as to coincide with the prior image location. Then, as depicted in FIG. 1E, the preplanned interventional procedure can be relatively promptly effected by merely causing the interventional device to retrace the earlier located optimal trajectory into the actual patient tissue. For example, in the case of a simple needle 20, once the clampable jig members have been properly positioned, the needle may simply be linearly slid along the desired trajectory into the patient tissue to some previously noted desired depth dimension marker 26. Preferably, the actual procedure is also monitored in real-time by the attending physician through the use of conventional fluoroscopic MRI displays.

Figure 2:
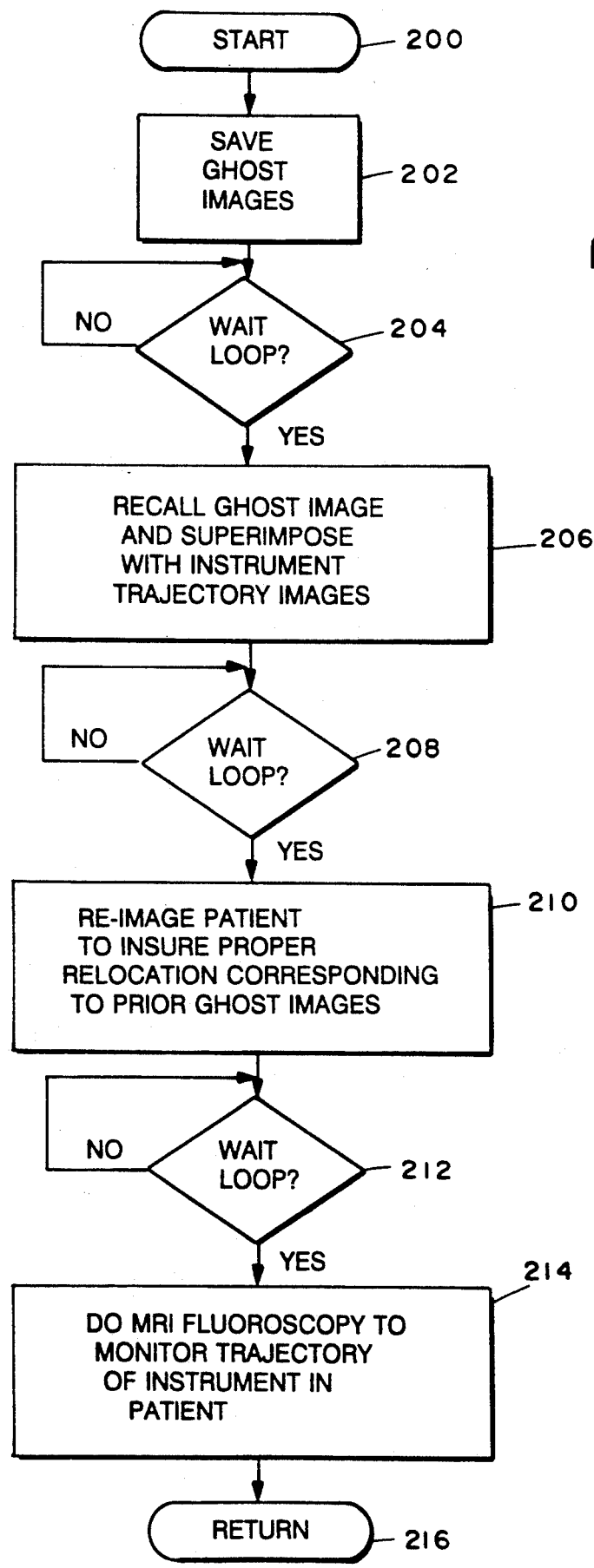
FIG. 2 is a simplified flowchart of an exemplary interventional process in accordance with this invention.

FIG. 2 schematically depicts an exemplary interventional medical procedure using the novel method and apparatus of this invention. For example, after entry at 200, suitable ghost images are saved at 202 before a wait loop 204 is entered to provide suitable time for removing the patient anatomy from the image volume. Progression from step 202 to the wait loop 204 can be effected upon the actuation of a suitable key or key sequence by the attending physician as should be appreciated.

Similarly, when the attending physician is ready to progress from wait loop 204, another key or key sequence actuation causes progression to step 206 where the previously acquired ghost image is recalled and superimposed with real time fluoroscopic MRI images (e.g., of the trial and error instrument trajectories). Thereafter, wait loop 208 is entered so as to provide time for removing the instrument from the image volume and reintroducing the patient to the image volume. Thereafter, at step 210, the patient anatomy is re-imaged to insure proper relocation corresponding to the prior ghost image locations of the anatomy. Then, a wait loop 212 may be entered, if desired, to permit the attending physician time for preparing the interventional device for the actual procedure or the like. Thereafter, while the actual interventional procedure is being performed, MRI fluoroscopy may be performed at step 214 so as to monitor the actual trajectory of the instrument within the patient tissue before return to traditional MRI control is made at 216.

Figure 3:
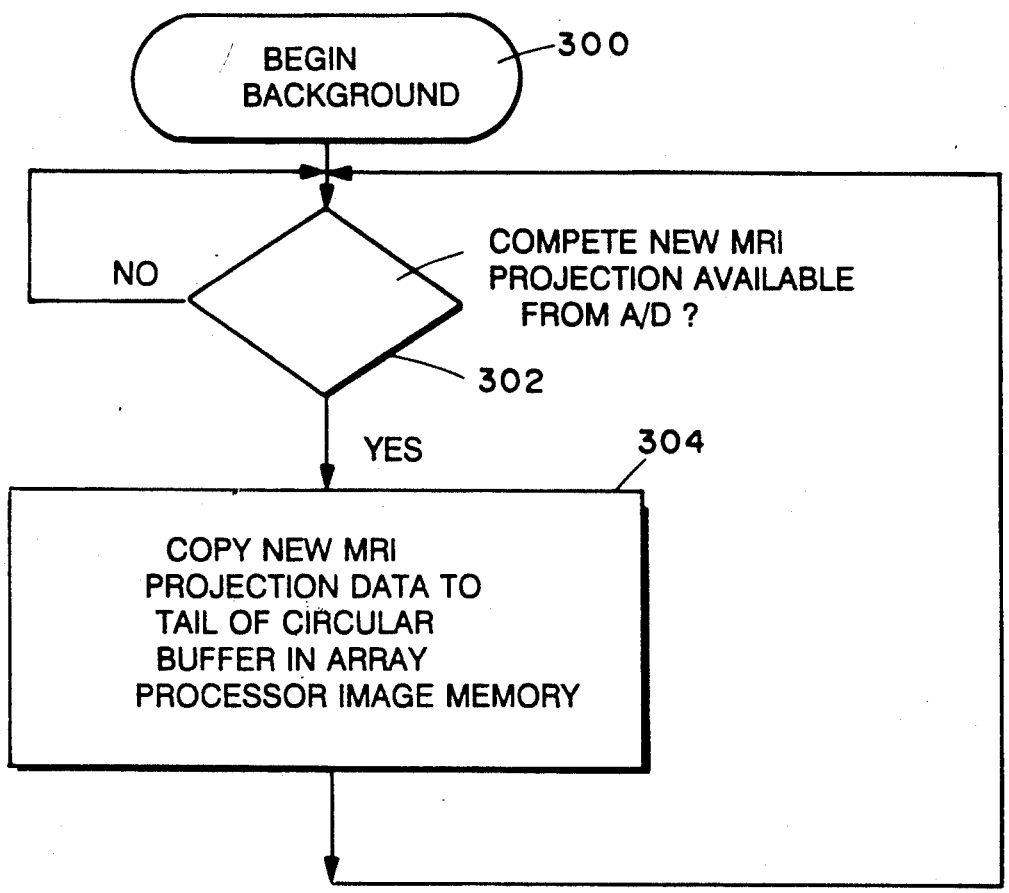
FIGS. 3, 4A and 4B are simplified flowcharts of relevant computer program segments for the control/imaging processors of an MRI system to use in effecting an exemplary embodiment of this invention.

During fluoroscopic MRI, a typical background function is continuously performed as depicted in FIG. 3. Here, upon entry at 300, a test is made at 302 to see if a complete new set of MRI projection data are yet available from an analog-to-digital converter. If so, then the new MRI projection data is copied to the tail of a circular buffer in an array processor image memory at 304 before control is returned to the test loop at 302. Of course, as will be appreciated, an actual implementation of this loop would include other housekeeping functions such as, for example, testing for a possible commanded exit from the fluoroscopic mode of operation. However, the existence of this basic background function permits the MRI system to memorize a prior image and to later recall it.

Figure 4A:
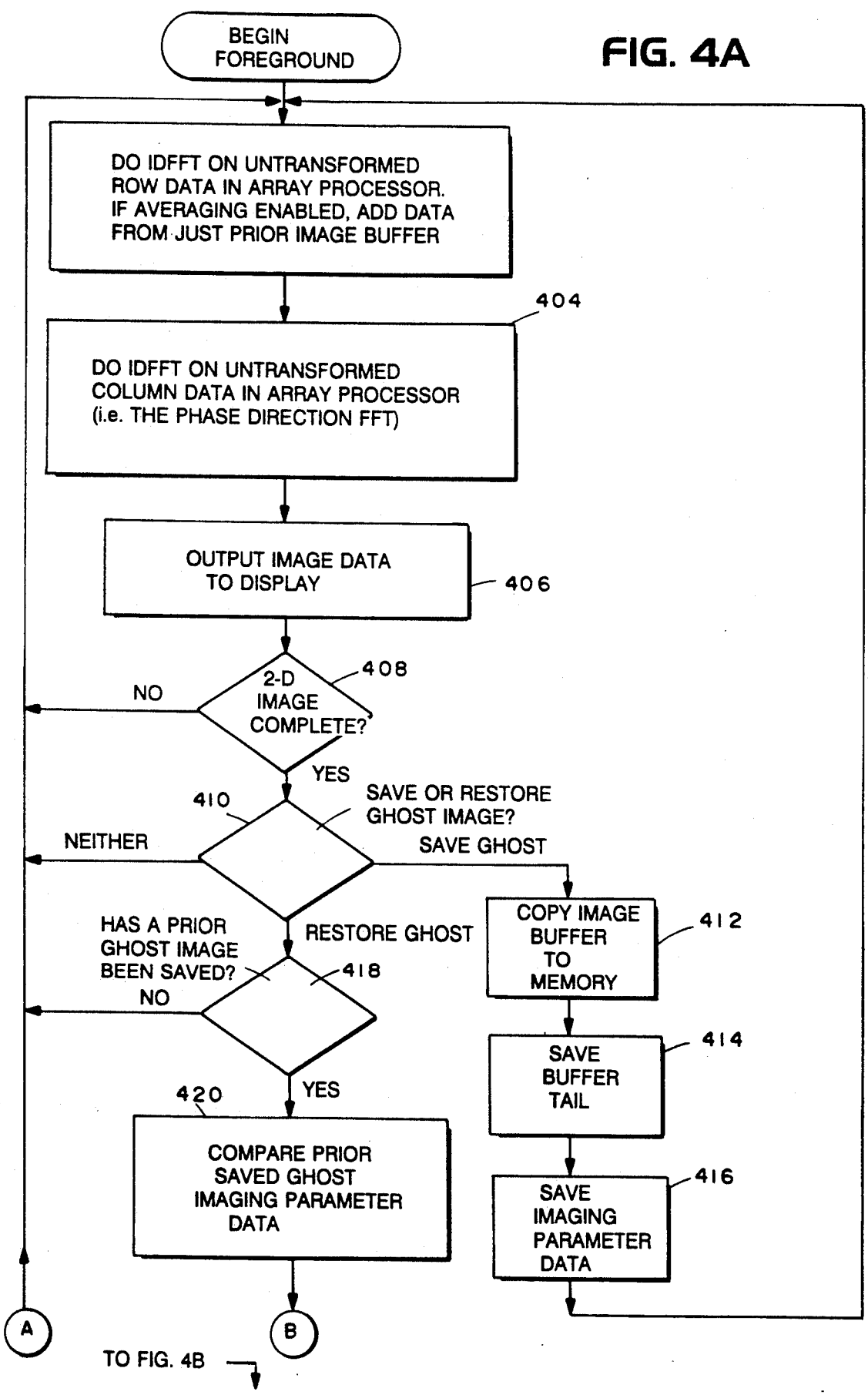
Figure 4B:
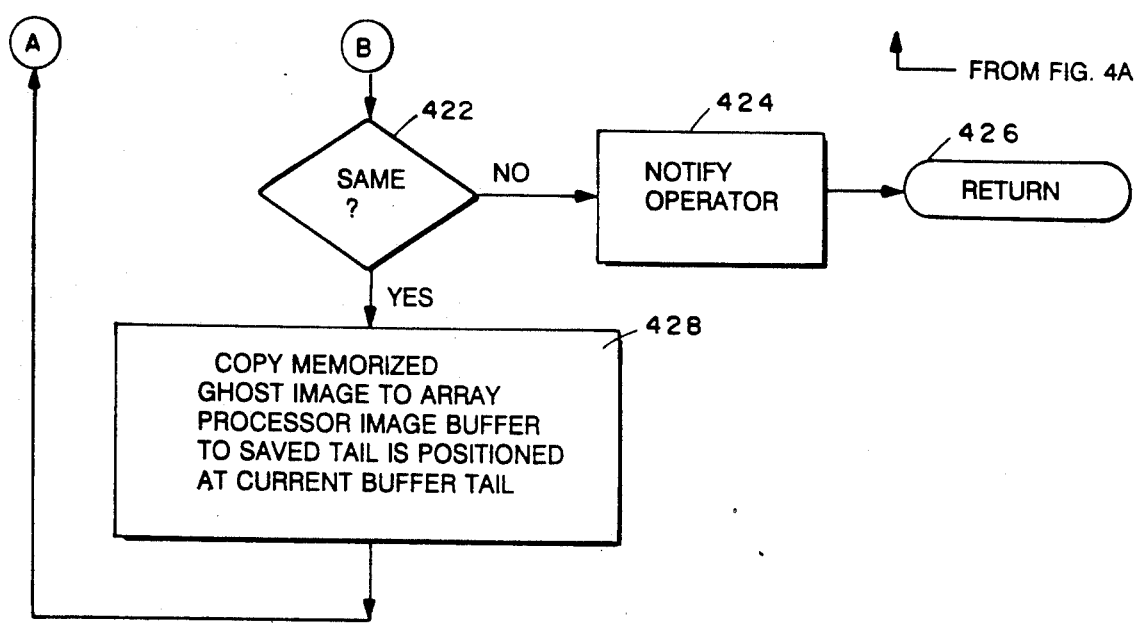

An exemplary controlled foreground program is depicted at FIGS. 4A-4B. Here, after entry at 400, the usual one dimensional FFT is performed at 402 on raw untransformed data in the array processor memory. If the "averaging" mode is enabled (as it will be during the interventional planning stages of this invention), then data is added from the just prior image buffer. Thereafter, the usual one dimensional FFT in the orthogonal (i.e., the phase direction in k-space) is performed at step 404. The resulting two dimensionally transformed data then represents a two-dimensional array of grey scale display pixel values which are output as image data for display at 406. A test is made at 408 for completeness of the image display data. Once a complete set of image data is available, control is transferred to 410 where a test is made as to whether the operator desires to save or restore a ghost image. If neither, then the ongoing fluoroscopic MRI imaging process is continued. On the other hand, if the current image is to be saved as a "ghost" image for future use, then the ghost image data is copied at 412 to an image buffer memory, the buffer tail is saved at 414 and relevant imaging parameter data (e.g., image size, scan directions, image offsets, phase ordering, spatial FID encoding, AFI information, etc.) is also saved at 416 before control is returned to the usual fluoroscopic MRI processes.

On the other hand, if a previously saved ghost is to be restored, then control is passed from the test at 410 to a further test at 418 just to be sure that a prior ghost image has indeed been saved and is available. If not, control is again returned to the usual MRI fluoroscopic processes. However, if the prior ghost image has been saved, then the saved ghost imaging parameter information is compared to current imaging parameter information at 420. If they are not the same as tested at 422, then the operator is notified at 424 and a return is made at 426. If the imaging parameter data does favorably compare, then the memorized ghost image is copied at 428 into the array processor image buffer so that the saved buffer tail is positioned at the current buffer tail position (i.e., so that in the averaging mode, the ghost image will be superimposed with the ongoing fluoroscopic MRI image) before control is passed back to the usual MRI fluoroscopic process as depicted in FIGS. 4A-4B.

In this simple exemplary embodiment, restoring a ghost image clears the array processor image buffer of all current image data. As new image data is acquired, data in the array processor buffer that came from the ghost image gradually will be replaced. To insure that the ghost image remains visible for more than one image cycle, the averaging mode must be turned "on." A saved ghost image can be restored as many times as desired. In the simple exemplary embodiment here depicted, when a second ghost image is saved, the first one is lost. However, as should be apparent to those skilled in the art, suitable modifications to the apparatus/software of conventional MRI systems can provide considerably more flexibility and possibilities. For example, multiple ghost images could be saved and selectively recalled and superimposed as instructed by the operator.

Using this invention, it is believed possible to achieve device replacement accuracies within tissue on the order of about 1 to 2 millimeters while at the same time greatly increasing the efficiency and safety of the interventional procedures. As previously noted, there are inherent inaccuracies in MR images. For example, there are inherent inaccuracies caused by inhomogeneities in the field of the main magnet, non-uniformities in imposed magnetic gradient fields, and distortions in the magnetic field produced by the object being imaged. The first order inaccuracies are caused by non-uniformities in the main magnet and/or gradient fields. These inaccuracies are substantially alleviated by this invention. Second order distortions related to magnetic field distortions caused by the imaged tissue/instrument are naturally minimized by the use of fluoroscopic MRI imaging sequences since such fluoroscopic sequences inherently use short TR, TE and data acquisition windows.

Although this invention has been only briefly described in connection with one or more exemplary embodiments, those skilled in the art will realize that many variations and modifications may be made in such exemplary embodiment(s) while yet retaining many of the novel features and advantages of this invention. Accordingly, all such variations and modifications are intended to be included within the scope of the appended claims.

What is claimed is:

1. An MRI method comprising:
   positioning an interventional device within the patient image volume of an MRI system while viewing real-time fluoroscopic MR images of such device superimposed on a saved prior image of patient anatomy that was earlier located within the same image volume.

2. An MRI method as in claim 1 further comprising:
   defining a repeatable trajectory to at least one predetermined position of the interventional device within the image volume;
   locating patient anatomy within the image volume to correspond with that of the saved prior image; and
   re-introducing said interventional device into the image volume and into the patient anatomy along said repeatable trajectory to said at least one predetermined position.

3. An MRI method as in claim 2 wherein during said re-introducing step, the movement of said interventional device within the patient anatomy is subjected to real-time fluoroscopic MRI.

4. An MRI method comprising:
   superimposing a prior saved image of a first physical field with real-time fluoroscopic MR images of a second physical field.

5. An MRI method as in claim 4 wherein said first physical field comprises a patient anatomy and said second physical field comprises an interventional device.

6. An MRI method as in claim 4 wherein said first physical field comprises an interventional device and said second physical field comprises a patient anatomy.

7. An MRI method as in claim 4, 5 or 6 further comprising:
   thereafter generating real-time fluoroscopic MR images of said first physical field as it physically merges with said second physical field.

8. An MRI method for facilitating the safe introduction of interventional devices into patient anatomy, said method comprising:
   placing patient anatomy within the image volume of an MRI system;
   creating and saving an MR image of said patient anatomy;
   removing said patient anatomy from the image volume;
   locating a desired trajectory for an interventional device within said image volume while superimposing the saved MR image of said patient anatomy with real-time fluoroscopic MR images of the interventional device;
   removing said interventional device from the MR image of the patient anatomy while retaining an ability to retrace said desired trajectory;
   returning said patient anatomy to the image volume in substantial registry with its earlier position at the time the saved MR image was created; and
   introducing said interventional device into said patient anatomy along said desired trajectory.

9. An MRI method as in claim 8 wherein, during said introducing step, MRI fluoroscopy is utilized to provide substantially real time images of said patient anatomy and of said interventional device as it retraces said desired trajectory.

10. An MRI method as in claim 8 wherein, during said locating step, said interventional device is at least partly loaded with an MR-visible fluid.

11. An MRI method as in claim 8 wherein, during said locating step, said interventional device is at least partly surrounded by an MR-visible fluid.

12. An MRI method as in claim 8 wherein said interventional device is mounted for movement within an adjustable guiding jig which can be adjusted to at least partially define said desired trajectory and to thereafter facilitate retracing of that same trajectory.

13. An MRI method as in claim 8 wherein said interventional device is used in a stereotatic procedure coordinated with a stereotatic frame affixed to the patient anatomy.

14. An MRI method as in claim 8 wherein said interventional device is used to withdraw patient tissue for biopsy.

15. An MRI method as in claim 8 wherein said interventional device is used to impart treatment to tissues within said patient anatomy.

16. An MRI method as in claim 8 performed with an MRI system having a main magnet structure which is openly accessible from a lateral side of the patient anatomy.

17. An MRI method as in claim 8 wherein said returning step includes creating new MR images of the patient anatomy and superimposing same with the earlier saved image of the patient anatomy.

18. An MRI method as in claim 8 wherein said locating step includes plural trial attempts to locate trajectories for the interventional device reusing the same superimposed saved image of the patient anatomy for each trial and a selection of one such trajectory as the optimum and desired trajectory.

19. An MRI apparatus comprising:
   an open structure background MRI magnet allowing lateral access to a patient imaging volume for performance, of interventional procedures; and
   means for positioning an interventional device within the patient image volume of an MRI system while viewing real-time fluoroscopic MR images of such device superimposed on a saved prior image of patient anatomy that was earlier located within the same image volume.

20. An MRI apparatus as in claim 19 further comprising:
   means for defining a repeatable trajectory to at least one predetermined position of the interventional device within the image volume;

means for locating patient anatomy within the image volume to correspond with that of the saved prior image; and means for re-introducing said interventional device into the image volume and into the patient anatomy along said repeatable trajectory to said at least one predetermined position.

21. An MRI apparatus as in claim 20 including means for performing real-time fluoroscopic MRI within said patient anatomy of said interventional device during said operation of said means for re-introducing.

22. An MRI apparatus comprising:
an open structure background MRI magnet allowing lateral access to a patient imaging volume for performance of interventional procedures; and
means for superimposing a prior saved image of a first physical field with real-time fluoroscopic MR images of a second physical field.

23. An MRI apparatus as in claim 22 wherein said first physical field comprises a patient anatomy and said second physical field comprises an interventional device.

24. An MRI apparatus as in claim 22 wherein said first physical field comprises an interventional device and said second physical field comprises a patient anatomy.

25. An MRI apparatus as in claim 22, 23 or 24 further comprising:
means for generating real-time fluoroscopic MR images of said first physical field as it physically merges with said second physical field.

26. An MRI apparatus for facilitating the safe introduction of interventional devices into patient anatomy, said apparatus comprising:
means for placing patient anatomy within the image volume of an MRI system;
means for creating and saving an MR image of said patient anatomy;
means for removing said patient anatomy from the image volume;
means for locating a desired trajectory for an interventional device within said image volume while superimposing the saved MR image of said patient anatomy with real-time fluoroscopic MR images of the interventional device;
means for removing said interventional device from the MR image of the patient anatomy while retaining an ability to retrace said desired trajectory;
means for returning said patient anatomy to the image volume in substantial registry with its earlier position at the time the saved MR image was created; and
means for introducing said interventional device into said patient anatomy along said desired trajectory.

27. An MRI apparatus as in claim 26 including means for performing MRI fluoroscopy to provide substantially real time images of said patient anatomy and of said interventional device as it retraces said desired trajectory.

28. An MRI apparatus as in claim 26 wherein said interventional device is at least partly loaded with an MR-visible fluid when used to locate said trajectory.

29. An MRI apparatus as in claim 26 wherein said interventional device is at least partly surrounded by an MR-visible fluid when used to locate said trajectory.

30. An MRI apparatus as in claim 26 wherein said interventional device is mounted for movement within an adjustable guiding jig which can be adjusted to at least partially define said desired trajectory and to thereafter facilitate retracing of that same trajectory.

31. An MRI apparatus as in claim 26 wherein said interventional device is part of a stereotatic apparatus coordinated with a stereotatic frame affixed to the patient anatomy.

32. An MRI apparatus as in claim 26 wherein said interventional device is capable of withdrawing patient tissue for biopsy.

33. An MRI apparatus as in claim 26 wherein said interventional device capable of imparting treatment to tissues within said patient anatomy.

34. An MRI apparatus as in claim 26 including means for creating new MR images of the patient anatomy and superimposing same with the earlier saved image of the patient anatomy.

* * * * *